United States Patent
Echigo et al.

(10) Patent No.: US 7,157,606 B2
(45) Date of Patent: Jan. 2, 2007

(54) PROCESS FOR PRODUCING AN AMINO COMPOSITION

(75) Inventors: Masatoshi Echigo, Kanagawa (JP); Hisayuki Kuwahara, Kanagawa (JP); Takeshi Koyama, Kanagawa (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 191 days.

(21) Appl. No.: 10/911,478

(22) Filed: Aug. 5, 2004

(65) Prior Publication Data

US 2005/0038298 A1 Feb. 17, 2005

(30) Foreign Application Priority Data

Aug. 13, 2003 (JP) ............................. 2003-293133

(51) Int. Cl.
*C07C 209/60* (2006.01)
(52) U.S. Cl. ....................................... 564/485; 564/408
(58) Field of Classification Search ................ 564/408, 564/485
See application file for complete search history.

(56) References Cited

U.S. PATENT DOCUMENTS 4,034,040 A 7/1977 Cronin et al.
4,302,603 A * 11/1981 Pez ............................ 564/485
6,562,934 B1 * 5/2003 Yonehama et al. .......... 528/122
2002/0055605 A1 5/2002 Yonehama et al.

FOREIGN PATENT DOCUMENTS

EP 1 188 740 A2 3/2002

OTHER PUBLICATIONS

Narita, T. et al., "Stereospecific Addition Reaction between Butadiene and Amines" *Bulletin of the Chemical Society of Japan*, vol. 46, No. 4, pp. 1242 to 1246, 1973.

* cited by examiner

*Primary Examiner*—Brian Davis
(74) *Attorney, Agent, or Firm*—Wenderoth, Lind & Ponack, L.L.P.

(57) ABSTRACT

The process for producing an amino composition of the present invention by addition reaction of a polyamine with an alkenyl group-containing compound wherein said polyamine is reacted preliminarily with a strongly basic catalyst to produce a reaction mixture comprising a reaction intermediate and then an alkenyl group-containing compound is added to the reaction mixture to proceed the addition reaction provides an amino composition having stable properties.

20 Claims, No Drawings

PROCESS FOR PRODUCING AN AMINO COMPOSITION

BACKGROUND OF THE INVENTION

1) Field of the Invention

The present invention relates to a process for producing an amino composition by an addition reaction between a polyamine and an alkenyl group-containing compound. The amino composition obtained by the process according to the present invention has reactivity with epoxy resins, isocyanates and the like, and is useful as curing agents for epoxy resins or chain extenders for polyurethane resins.

2) Related Art

An amino composition obtained by the addition reaction of a polyamine with an alkenyl group-containing compound is known to be characterized in that it has low viscosity and its content of unreacted polyamine is relatively low. For instance, an epoxy resin composition which contains curing agents for epoxy resins comprising said amino composition provides an excellent property of an epoxy resin cured product. Therefore, said amino composition has an excellent industrial availability.

The process for producing the above-mentioned amino composition comprising the step of addition reaction between a polyamine and an alkenyl group-containing compound in the presence of a strongly basic catalyst has been publicly known (Japanese Patent Kokai No. 2002-161076).

According to the process directed in Japanese Patent Kokai No. 2002-161076, the addition reaction is conducted by firstly contacting a polyamine with catalysts and then an alkenyl group-containing compound is added immediately after increasing the temperature of the reaction mixture.

In this case, the point of termination of the addition reaction is determined by measuring the content of unreacted alkenyl group-containing compounds in the reaction mixture. Namely, when the content of unreacted alkenyl group-containing compounds becomes under a certain amount, the addition reaction is regarded to be completed. More specifically, the reaction time is determined so that the content of unreacted alkenyl group-containing compounds becomes not more than 1% by weight.

However, the above-mentioned process has some defects. For example, it often takes long time until the reaction is completed. More specifically, it takes more than 30 minutes from the finish of supplying an alkenyl group-containing compound up to the time that the content of unreacted alkenyl group-containing compounds becomes not more than 1% by weight.

Further, the reaction time often varies widely. Moreover, the content of unreacted alkenyl group-containing compounds sometimes becomes difficult to be under 1% by weight and the reaction is not completed.

Extension of the reaction time causes some defects such as the formation of an unfavorable polymer of alkenyl group-containing compounds as a by-product.

The formation of a polymer of alkenyl group-containing compounds and/or the presence of residual unreacted alkenyl group-containing compounds cause the lack of stability in properties of the obtainable amino composition.

SUMMARY OF THE INVENTION

An object of the present invention is to provide a process for producing an amino composition by an addition reaction of a polyamine with an alkenyl group-containing compound, whereby an amino composition having stable properties is obtainable.

As a result of extensive studies, the inventors have found that a process comprising a step of firstly conducting a preliminary reaction between a polyamine and a strongly basic catalyst to a certain degree and then adding an alkenyl group-containing compound to the reaction mixture to conduct an addition reaction can solve the above problem, and have accomplished the present invention.

Therefore, the present invention provides a process for producing an amino composition described in the following 1) to 12).

1) A process for producing an amino composition by an addition reaction between a polyamine and an alkenyl group-containing compound in the presence of a strongly basic catalyst, which comprises the first step wherein a preliminary reaction between a polyamine and a strongly basic catalyst is conducted to obtain a reaction mixture, and the second step wherein an alkenyl group-containing compound is added to said reaction mixture to conduct an addition reaction.

2) The process according to (1), which comprises said first step wherein a preliminary reaction between a polyamine and a strongly basic catalyst is conducted to obtain a reaction mixture comprising a reaction intermediate, and said second step wherein an alkenyl group-containing compound is added to said reaction mixture comprising said reaction intermediate to conduct an addition reaction.

3) The process according to (2), wherein an alkenyl group-containing compound is added to said reaction mixture comprising a reaction intermediate after the concentration of said reaction intermediate in said reaction mixture becomes not less than 0.001 mol based upon 1 mol of said polyamine.

4) The process according to (3), wherein the concentration of said reaction intermediate is calculated from the absorbance of an absorption peak obtained by an infrared spectroscopic analysis with said reaction mixture which had been observed at 1650 to 1580 $cm^{-1}$ before the preliminary reaction and then shifted to a position having 20 to 25 $cm^{-1}$ lower wavenumber after the preliminary reaction.

5) The process according to (1) to (4), wherein the reaction temperature of said preliminary reaction between a polyamine and a strong basic catalyst is 10 to 140° C. and the reaction time thereof is 20 to 360 minutes.

6) The process according to (1) to (5), wherein said alkenyl group-containing compound is added to said reaction mixture in the form of divided supply or in the form of continuous supply.

7) The process according to (6), wherein said alkenyl group-containing compound is added to said reaction mixture in the form of divided supply in 3 to 500 portions.

8) The process according to (6), wherein said alkenyl group-containing compound is added to said reaction mixture in the form of continuous supply taking 10 minutes to 20 hours.

9) The process according to (1) to (8), wherein said polyamine is selected from the group consisting of polyamines represented by the formula (1) wherein A is a phenylene group or a cyclohexylene group.

$$H_2N-CH_2-A-CH_2-NH_2 \quad (1)$$

10) The process according to (1) to (8), wherein said polyamine is selected from the group consisting of polyamines represented by the formula (2) wherein n is 1 to 5.

$$H_2N-(CH_2CH_2NH)_n-H \quad (2)$$

11) The process according to (1) to (8), wherein said polyamine is selected from the group consisting of cyclic aliphatic polyamines having at least nine carbon atoms, at least two amino groups and at least three active hydrogen atoms derived from said amino groups.
12) The process according to (1) to (8), wherein said polyamine is selected from the group consisting of polyoxyalkylenepolyamines.
13) The process according to (1) to (12), wherein said alkenyl group-containing compound is a compound having 2 to 10 carbon atoms.

DETAILED DESCRIPTION OF THE INVENTION

The process for producing an amino composition of the present invention comprises an addition reaction of a polyamine and an alkenyl group-containing compound in the presence of a strongly basic catalyst characterized in that firstly a preliminary reaction between a polyamine and a strongly basic catalyst is conducted to obtain a reaction mixture and then an alkenyl group-containing compound is added to the reaction mixture to conduct an addition reaction.

Suitable polyamines to be used in the present invention include a polyamine represented by the formula (1) wherein A is a phenylene group or a cyclohexylene group, a polyamine represented by the formula (2) wherein n is 1 to 5, a cyclic aliphatic polyamine having at least nine carbon atoms, at least two amino groups and at least three active hydrogen atoms derived from said amino groups, and a polyoxyalkylenepolyamine.

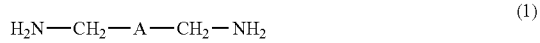

$$H_2N-CH_2-A-CH_2-NH_2 \quad (1)$$

$$H_2N-(CH_2CH_2NH)_n-H \quad (2)$$

Suitable polyamines represented by the formula (1) include orthoxylylenediamine, metaxylylenediamine, paraxylylenediamine, 1,2-bis (aminomethyl) cyclohexane, 1,3-bis (aminomethyl) cyclohexane and 1,4-bis (aminomethyl) cyclohexane.

Suitable polyamines represented by the formula (2) include ethylenediamine, diethylenetriamine, triethylenetetramine, tetraethylenepentamine and pentaethylenehexamine.

Suitable cyclic aliphatic polyamines having at least nine carbon atoms, at least two amino groups and at least three active hydrogen atoms derived from said amino groups include menthanediamine, isophoronediamine, diaminodicyclohexylmethane, bis(4-amino-3-methylcyclohexyl) methane, N-aminomethylpiperazine, norbornanediamine and bis(aminomethyl)tricyclodecane.

Suitable polyoxyalkylenepolyamines include polyoxyalkylenediamines such as polyoxyethylenediamine, polyoxypropylenediamine, polyoxytetramethylenediamine and poly(oxyethylene-oxypropylene)diamine; and polyoxyalkylenetriamines such as polyoxyethylenetriamine and polyoxypropylenetriamine.

Examples of the alkenyl group-containing compounds to be used in the present invention include any kind of compounds having at least one alkenyl group, namely an unsaturated hydrocarbon compounds. Among them, an unsaturated hydrocarbon compounds having a carbon number of 2 to 10 are preferable.

Suitable unsaturated hydrocarbon compounds having 2 to 10 carbon atoms include ethylene, propylene, butene, butadiene, pentene, hexene, heptene, octene, nonene, decene, isobutylene, 2-pentene, 3-methyl-1-butene, 2-methyl-2-butene, 2,3-dimethyl-2-butene, cyclohexene, cyclohexadiene, styrene and divinylbenzene.

In the process for producing an amino composition of the present invention, a catalyst exhibiting strong basicity is used. The strongly basic catalyst includes alkaline metal compounds such as alkaline metals, alkaline metal amides and alkylated alkaline metals.

Suitable alkaline metals include metallic lithium, metallic sodium and metallic potassium. Suitable alkaline metal amides include lithium amide (LiNH$_2$), lithium diisopropyl amide and sodium amide. Suitable alkylated alkaline metals include methyl lithium and butyl lithium.

Other suitable catalysts exhibiting strong basicity include lithium methylate, lithium ethylate, sodium ethylate, sodium methylate and potassium methylate.

Among them, alkaline metal amides are preferable and lithium amide is more preferable.

The process for producing an amino composition having stable properties of the present invention comprises firstly conducting a preliminary reaction between a polyamine and a strongly basic catalyst to obtain a reaction mixture, and then adding an alkenyl group-containing compound to the reaction mixture to conduct an addition reaction.

More preferable, the process for producing an amino composition of the present invention comprises conducting a preliminary reaction between a polyamine and a strongly basic catalyst to produce a reaction mixture comprising a reaction intermediate formed from the polyamine and the catalyst, and then adding an alkenyl group-containing compound to the reaction mixture after a certain amount of the reaction intermediate has been formed.

According to the process in which the alkenyl group-containing compound is added in the reaction mixture after producing a reaction intermediate by the preliminary reaction of the polyamine and the catalyst, the polyamine and the alkenyl group-containing compound can be contacted in the reaction mixture after the reactivity of active hydrogen atoms of the polyamine is elevated sufficiently. Therefore, the addition reaction between the polyamine and the alkenyl group-containing compound can be facilitated With regard to the method for making a decision whether or not the reaction between the polyamine and the strongly basic catalyst has made progress to a certain degree sufficient enough to elevate the reactivity of active hydrogen atoms of the polyamine, though it is not restricted to a specific method, it preferably can be determined whether or not the concentration of the reaction intermediate in the reaction mixture after the preliminary reaction is not less than 0.001 mol, more preferably 0.002 mol based upon 1 mol of the polyamine.

That is, when the concentration of the reaction intermediate is 0.001 mol or more, it can be determined that the polyamine and the catalyst has been reacted sufficiently.

Thus, the more preferable method of the present invention comprises conducting a preliminary reaction between the polyamine and the strongly basic catalyst to obtain a reaction mixture wherein the concentration of the reaction intermediate formed by the polyamine and the catalyst becomes 0.001 mol or more based upon 1 mol of the polyamine, and then adding an alkenyl group-containing compound to the reaction mixture comprising the reaction intermediate to conduct the addition reaction.

The formation of the reaction intermediate can be verified by infrared (IR) spectroscopic analyses. After the preliminary reaction between the polyamine and the strongly basic catalyst, an IR spectroscopic analysis is carried out with a portion sampled from the reaction mixture obtained by said preliminary reaction.

An absorption peak is observed in the range of 1650 to 1580 cm$^{-1}$ with the polyamine before the preliminary reaction (hereinafter, "absorption peak (A)"), which, after the preliminary reaction, moves to a shifted position having 20–25 cm$^{-1}$ lower wavenumber than that of the absorption peak (A). With the aid of the calibration curve, the concentration of the reaction intermediate can be calculated from the absorbance of a new absorption peak (hereinafter, "absorption peak (B)") observed at 20–25 cm$^{-1}$ lower position than the absorption peak (A).

The absorption peak (A) observed at 1650–1580 cm$^{-1}$ with the polyamine before the preliminary reaction can be assigned to an absorption derived from an N—H bending (scissoring) vibration of the polyamine before reacting with the strong basic catalyst. This absorption peak (A) appears at slightly different positions within the range of 1650–1580 cm$^{-1}$ depending on the variety of polyamines.

As the preliminary reaction proceeds to form a reaction intermediate which is a complex compound of the polyamine and the strong basic catalyst, the absorption peak (A) disappears, and a new absorption peak (B) appears at a 20–25 cm$^{-1}$ lower position than that of the absorption peak (A). Therefore, the new absorption peak (B) is observed in the range of 1630–1555 cm$^{-1}$ after the formation of a reaction intermediate.

The absorbance of the new absorption peak (B) increases as the preliminary reaction proceeds and the concentration of the reaction intermediate in the reaction mixture increases.

Therefore, the concentration of the reaction intermediate in the reaction mixture can be calculated by measuring the absorbance of the newly observed absorption peak (B) and drawing in advance a calibration curve in the ordinary way.

For instance, in the case of the preliminary reaction between lithium amide as a strongly basic catalyst and metaxylylenediamine as a polyamine, the absorption peaks at 3363 and 3264 cm$^{-1}$ (asymmetrical and symmetrical N—H stretching vibration) and 1606 cm$^{-1}$ (N—H bending (scissoring) vibration) which are observed with metaxylylenediamine before the preliminary reaction shift to 3342 and 3258 cm$^{-1}$ (asymmetrical and symmetrical N—H stretching vibration) and 1581 cm$^{-1}$ (N—H bending (scissoring) vibration) respectively as the preliminary reaction proceeds. This indicates the formation of the reaction intermediate.

In the above case, the amount of the formed reaction intermediate can be found by attending to the absorbance of the absorption peak at 1581 cm$^{-1}$ (N—H bending (scissoring) vibration) observed in the infrared spectroscopic data with the reaction mixture. As the absorbance of the absorption peak at 1581 cm$^{-1}$ increases in proportion to the amount of the formed reaction intermediate, the amount of the formed reaction intermediate can be determined by preparing a calibration curve for the absorption peak at 1581 cm$^{-1}$ previously.

When the amount of the reaction intermediate in the reaction mixture is not less than 0.001 mol based upon 1 mol of the polyamine, the addition reaction is facilitated.

In the case that the polyamine is 1,3-bis(aminomethyl) cyclohexane, the absorption peak at 1600 cm$^{-1}$ (N—H bending (scissoring) vibration) observed before the preliminary reaction moves to 1575 cm$^{-1}$ as the preliminary reaction proceeds and the reaction intermediate is formed.

When the polyamine is norbornanediamine, the absorption peak at 1600 cm$^{-1}$ (N—H bending (scissoring) vibration) observed before the preliminary reaction moves to 1575 cm$^{-1}$ as the reaction intermediate is formed.

When the polyamine is isophoronediamine, the absorption peak at 1598 cm$^{-1}$ (N—H bending (scissoring) vibration) observed before the preliminary reaction moves to 1573 cm$^{-1}$ as the reaction intermediate is formed.

In the same way, the absorption peak at 1597 cm$^{-1}$ with diethylenetriamine moves to 1572 cm$^{-1}$, the absorption peak at 1596 cm$^{-1}$ with triethylenetetramine moves to 1572 cm$^{-1}$, the absorption peak at 1591 cm$^{-1}$ with polyoxypropylenediamine moves to 1568 cm$^{-1}$, and the absorption peak at 1600 cm$^{-1}$ with polyoxyethylenediamine moves to 1575 cm$^{-1}$.

Though the chemical structure of the reaction intermediate here is not necessarily be determined precisely, it is presumed to be a complex compound wherein 1 mol of polyamine is combined with 1 or 2 mol of strongly basic catalyst. The addition reaction of a polyamine and an alkenyl group-containing compound in the presence of a strong basic catalyst of the present invention is presumably promoted by the reaction mechanism represented by the following formulas;

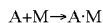

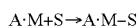

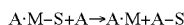

wherein A is a polyamine, M is a strongly basic catalyst, S is an alkenyl group-containing compound, A·M is a complex compound which is a reaction intermediate obtained by the preliminary reaction between the polyamine and the strongly basic catalyst, A-S is an addition reaction product between the polyamine and the alkenyl group-containing compound.

The reaction mechanism of the addition reaction of a polyamine with an alkenyl group-containing compound in the presence of a strongly basic catalyst itself is known by Bulletin of the Chemical Society of Japan, Vol. 46, 1242–1246(1973), or Bulletin of the Chemical Society of Japan, Vol. 46, 3825–3828(1973).

The amount of catalyst to be used for the preliminary reaction of a polyamine with a strongly basic catalyst is preferably 0.05 to 5% by weight, more preferably 0.1 to 3% by weight based upon the total weight of the starting materials.

When the amount of the catalyst is less than 0.05% by weight, the reaction rate of the addition reaction between the polyamine and the alkenyl group-containing compound may become extremely low. On the other hand, the increased amount of the catalyst more than 5% by weight may not be economically advantageous because the reaction rate is scarcely increased.

The preferable reaction temperature of the preliminary reaction between the polyamine and the strongly basic catalyst is 10 to 140° C., more preferably 50 to 120° C. When the reaction temperature is lower than 10° C., progress of the reaction between the polyamine and the strongly basic catalyst may be too slow. On the other hand, the increased reaction temperature higher than 140° C. may not be economically advantageous because the reaction rate is scarcely increased.

The preferable reaction time of the preliminary reaction between the polyamine and the strongly basic catalyst is 20 to 360 minutes, more preferably 30 to 120 minutes. When the reaction time is shorter than 20 minutes, the reaction between the polyamine and the strongly basic catalyst may not proceed sufficiently. On the other hand, the increased reaction time longer than 360 minutes may not be economically advantageous because the reaction rate is scarcely increased.

The addition reaction by adding an alkenyl group-containing compound to the reaction mixture after the preliminary reaction between the polyamine and the strongly basic catalyst is usually carried out at the temperature of 50 to 150° C., more preferably 80 to 100° C.

When the reaction temperature of the addition reaction is lower than 50° C., the reaction rate of the addition reaction between the polyamine and the alkenyl group-containing compound may become too slow. On the other hand, when the reaction temperature of the addition reaction is higher than 150° C., a polymer of the alkenyl group-containing compounds may readily be formed as a by-product.

The addition reaction after the preliminary reaction between a polyamine and an alkenyl group-containing compound is carried out by adding an alkenyl group-containing compound to the reaction mixture preferably in the form of divided supply or continuous supply.

When the strongly basic catalyst, the polyamine and the alkenyl group-containing compound are added to the reaction mixture all at once to conduct an addition reaction, a rapid heat generation and/or a formation of a polymer of alkenyl group-containing compounds may occur.

In the case of adding the alkenyl group-containing compound to the reaction mixture in the form of divided supply, it is preferable to supply the alkenyl group-containing compound by dividing into 3 to 500 portions, more preferably 10 to 200 portions. When the alkenyl group-containing compound is supplied by dividing into less than 3 portions, a polymer of the alkenyl group-containing compounds may readily be formed. On the other hand, the divided supply into more than 500 portions may not be economically advantageous because the reaction condition is scarcely influenced. The method for the divided supply can be selected from known arts and is not limited.

In the case of adding the alkenyl group-containing compound to the reaction mixture in the form of continuous supply, the method of supply is not specifically limited and it can be selected from generally known methods such as a method wherein the alkenyl group-containing compound is added by using a dropping funnel, a method wherein the alkenyl group-containing compound is added by using a liquid transfer pump.

In either method of divided supply or continuous supply, the period of time for supplying the alkenyl group-containing compound is not specifically limited as far as the heat generation from the addition reaction of the alkenyl group-containing compound can be controlled. The preferable time for supply is 10 minutes to 20 hours, more preferably 30 minutes to 10 hours. When the time for supply is shorter than 10 minutes, a rapid heat generation may occur and the reaction may be beyond control. On the other hand, the time for supply longer than 20 hours may not be economically advantageous because the reaction condition is scarcely influenced. Especially in the case of divided supply, when the number of portions of division is small, the time for supply is preferable to be relatively long, and when the number of portions of division is large, the time for supply can be relatively short.

By keeping the reaction temperature as it is for 30 to 120 minutes after the completion of supplying the alkenyl group-containing compound, an amino composition having stable properties wherein the content of an unreacted alkenyl group-containing compound is not more than 1% by weight is obtained.

According to the process of the present invention, the residual content of unreacted alkenyl group-containing compounds is small after the completion of supplying the alkenyl group-containing compound, which causes that a polymer of the alkenyl group-containing compounds as an unfavorable by-product is not formed even if the reaction time after supplying the alkenyl group-containing compound becomes longer, for example the reaction time is longer than 30 minutes.

The reaction liquid obtained after the addition reaction contains an amino composition produced by said addition reaction and a strongly basic catalyst.

It is possible to remove the strongly basic catalyst from the reaction liquid by filtration. Filtration can be easily carried out by changing the alkaline metal amide previously to a readily removable salt thereof by adding acids such as hydrochloric acid, hydrogen chloride gas and acetic acid; alcohols such as methanol and ethanol; and water. For example, when alkaline metal amide is used as the catalyst, the alkaline metal amide is changed to a hydroxide thereof which is easy to filtrate by means of adding water.

The amino composition obtained by the process of the present invention is an addition product by the addition reaction between a polyamine and an alkenyl group-containing compound, and is a mixture of one or more amino compounds selected from the group consisting of the following amino compounds; a 1-addition product wherein 1 molecule of the alkenyl group-containing compound is reacted with 1 molecule of polyamine, a 2-addition product wherein 2 molecules of the alkenyl group-containing compound are reacted with 1 molecule of polyamine, a 3-addition product wherein 3 molecules of the alkenyl group-containing compound are reacted with 1 molecule of polyamine, and a 4-addition product wherein 4 molecules of the alkenyl group-containing compound are reacted with 1 molecule of polyamine.

That is, the amino composition of the present invention comprises compounds wherein from one to all of the active hydrogen atom(s) of the amino group(s) in 1 molecule of the polyamine are reacted with the alkenyl group of the alkenyl group-containing compound.

In addition, since the amino composition of the present invention is a product obtained by the addition reaction between the polyamine and the alkenyl group-containing compound, it usually is a mixture containing unreacted polyamines and the like additional to the compounds selected from the group of the above-mentioned amino compounds.

As mentioned above, the process for producing an amino composition of the present invention comprising a step of conducting a preliminary reaction between a polyamine and a strongly basic catalyst to obtain a reaction mixture and a step of adding an alkenyl group-containing compound to said reaction mixture to conduct an addition reaction provides a manufacturing method whereby an amino composition having stable properties is obtainable.

PREFERRED EMBODIMENT OF THE INVENTION

The present invention will be described in more detail below, referring to Examples which are not intended to limit the scope of the present invention.

EXAMPLE 1

817.2 g (6.0 mol) of metaxylylenediamine (Molecular Weight; 136.2) having an active hydrogen equivalent weight of 34, manufactured by Mitsubishi Gas Chemical Co., Inc., in Japan (hereinafter, "MXDA") and 2.9 g (0.13 mol) of lithium amide, a reagent manufactured by Merck KGaA, were charged to a 2 L (liter) flask equipped with an agitator, a thermometer, a nitrogen gas inlet, a dropping funnel and a condenser and its interior temperature was raised to 80° C. taking 15 minutes in a nitrogen gas stream with stirring.

Then, after stirring the reaction mixture for 30 minutes at 80° C., 625.2 g (6.0 mol) of styrene, a special grade reagent, manufactured by Wako Pure Chemical Industries, Ltd., in Japan was added thereto dropwise continuously for 2 hours while keeping the temperature at 80° C.

The concentration of reaction intermediate in the reaction mixture was calculated from the absorption at 1581 cm$^{-1}$ obtained by IR spectroscopic analysis with a sample taken from the reaction mixture just before the addition of styrene. As a result of the calculation, it was found that the concentration of the reaction intermediate in the reaction mixture just before the addition of styrene was not less than 0.001 mol based upon 1 mol of MXDA.

After completion of the dropwise addition of styrene, its interior temperature was maintained to 80° C. for 30 minutes.

Then, 23.4 g (1.3 mol) of distilled water as the amount of 10 times equal mole to the charged lithium amide was added thereto and stirred. After separating precipitates in the liquid in the flask by filtration, remained water was removed by vacuum distillation, whereby 1381.7 g of an amino composition (A) was obtained as a reaction product. The content of unreacted styrene in the amino composition (A) was 0.2% by weight and the content of unreacted MXDA was 15.8% by weight. The content of 1-addition product was 46.4% by weight, the content of 2-addition product was 33.9% by weight, and the content of 3-addition product was 3.9% by weight.

EXAMPLE 2

681.0 g (5.0 mol) of MXDA and 3.3 g (0.14 mol) of lithium amide were charged to a similar flask as the one used in Example 1, and its interior temperature was raised to 80° C. taking 15 minutes in a nitrogen gas stream with stirring.

Then, after stirring the reaction mixture for 30 minutes at 80° C., 651.3 g (6.25 mol) of styrene was added thereto dropwise continuously for 2.5 hours while keeping the temperature at 80° C.

The concentration of reaction intermediate in the reaction mixture was calculated from the absorption at 1581 cm$^{-1}$ obtained by IR spectroscopic analysis with a sample taken from the reaction mixture just before the addition of styrene. As a result of the calculation, it was found that the concentration of the reaction intermediate in the reaction mixture just before the addition of styrene was not less than 0.001 mol based upon 1 mol of MXDA.

After completion of the dropwise addition of styrene, its interior temperature was maintained to 80° C. for 30 minutes.

Then, 25.2 g (1.4 mol) of distilled water as the amount of 10 times equal mole to the charged lithium amide was added thereto and stirred. After separating precipitates in the liquid in the flask by filtration, remained water was removed by vacuum distillation, whereby 1271.2 g of an amino composition (B) was obtained as a reaction product. The content of unreacted styrene in the amino composition (B) was 0.2% by weight and the content of unreacted MXDA was 8.1% by weight. The content of 1-addition product was 39.5% by weight, the content of 2-addition product was 44.2% by weight, the content of 3-addition product was 7.9% by weight, and the content of 4-addition product was 0.3% by weight.

EXAMPLE 3

853.2 g (6.0 mol) of 1,3-bis(aminomethyl)cyclohexane, manufactured by Mitsubishi Gas Chemical Co., Inc., in Japan (hereinafter, "1,3-BAC") and 3.0 g (0.13 mol) of lithium amide were charged to a similar flask as the one used in Example 1, and its interior temperature was raised to 80° C. taking 15 minutes in a nitrogen gas stream with stirring.

Then, after stirring the reaction mixture for 120 minutes at 80° C., 625.2 g (6.0 mol) of styrene was added thereto dropwise continuously for 2 hours while keeping the temperature at 80° C.

The concentration of reaction intermediate in the reaction mixture was calculated from the absorption at 1575 cm$^{-1}$ obtained by IR spectroscopic analysis with a sample taken from the reaction mixture just before the addition of styrene. As a result of the calculation, it was found that the concentration of the reaction intermediate in the reaction mixture just before the addition of styrene was not less than 0.001 mol based upon 1 mol of 1,3-BAC.

After completion of the dropwise addition of styrene, its interior temperature was maintained to 80° C. for 60 minutes.

Then, 23.4 g (1.3 mol) of distilled water as the amount of 10 times equal mole to the charged lithium amide was added thereto and stirred. After separating precipitates in the liquid in the flask by filtration, remained water was removed by vacuum distillation, whereby 1409.7 g of an amino composition (C) was obtained as a reaction product. The content of unreacted styrene in the amino composition (C) was 0.2% by weight and the content of unreacted 1,3-BAC was 15.1% by weight. The content of 1-addition product was 54.2% by weight, the content of 2-addition product was 28.7% by weight, and the content of 3-addition product was 2.1% by weight.

EXAMPLE 4

711.0 g (5.0 mol) of 1,3-BAC and 3.4 g (0.15 mol) of lithium amide were charged to a similar flask as the one used in Example 1, and its interior temperature was raised to 80° C. taking 15 minutes in a nitrogen gas stream with stirring.

Then, after stirring the reaction mixture for 120 minutes at 80° C., 651.3 g (6.25 mol) of styrene was added thereto dropwise continuously for 2.5 hours while keeping the temperature at 80° C.

The concentration of reaction intermediate in the reaction mixture was calculated from the absorption at 1575 cm$^{-1}$ obtained by IR spectroscopic analysis with a sample taken from the reaction mixture just before the addition of styrene. As a result of the calculation, it was found that the concentration of the reaction intermediate in the reaction mixture just before the addition of styrene was not less than 0.001 mol based upon 1 mol of 1,3-BAC.

After completion of the dropwise addition of styrene, its interior temperature was maintained at 80° C. for 60 minutes.

Then, 27.0 g (1.5 mol) of distilled water as the amount of 10 times equal mole to the charged lithium amide was added thereto and stirred. After separating precipitates in the liquid in the flask by filtration, remained water was removed by vacuum distillation, whereby 1307.1 g of an amino composition (D) was obtained as a reaction product. The content of unreacted styrene in the amino composition (D) was 0.2% by weight and the content of unreacted 1,3-BAC was 8.3% by weight.

EXAMPLE 5

412.7 g (4.0 mol) of diethylenetriamine, a special grade reagent manufactured by Kanto Kagaku Co., in Japan (hereinafter, "DETA") and 2.5 g (0.11 mol) of lithium amide were charged to a similar flask as the one used in Example 1, and its interior temperature was raised to 80° C. taking 15 minutes in a nitrogen gas stream with stirring.

Then, after stirring the reaction mixture for 30 minutes at 80° C., 651.3 g (6.25 mol) of styrene was added thereto dropwise continuously for 2 hours while keeping the temperature at 80° C.

The concentration of reaction intermediate in the reaction mixture was calculated from the absorption at 1572 cm$^{-1}$ obtained by IR spectroscopic analysis with a sample taken from the reaction mixture just before the addition of styrene. As a result of the calculation, it was found that the concentration of the reaction intermediate in the reaction mixture just before the addition of styrene was not less than 0.001 mol based upon 1 mol of DETA.

After completion of the dropwise addition of styrene, its interior temperature was maintained at 80° C. for 30 minutes.

Then, 19.8 g (1.1 mol) of distilled water as the amount of 10 times equal mole to the charged lithium amide was added thereto and stirred. After separating precipitates in the liquid in the flask by filtration, remained water was removed by vacuum distillation, whereby 777.1 g of an amino composition (E) was obtained as a reaction product. The content of unreacted styrene in the amino composition (E) was 0.2% by weight and the content of unreacted DETA was 16.3% by weight. The content of 1-addition product was 37.3% by weight, and the content of 2-addition product was 37.2% by weight.

EXAMPLE 6

584.8 g (4.0 mol) of triethylenetetramine, a special grade reagent manufactured by Kanto Kagaku Co., in Japan (hereinafter, "TETA") and 3.0 g (0.13 mol) of lithium amide were charged to a similar flask as the one used in Example 1, and its interior temperature was raised to 80° C. taking 15 minutes in a nitrogen gas stream with stirring.

Then, after stirring the reaction mixture for 30 minutes at 80° C., 651.3 g (6.25 mol) of styrene was added thereto dropwise continuously for 2.5 hours while keeping the temperature at 80° C.

The concentration of reaction intermediate in the reaction mixture was calculated from the absorption at 1572 cm$^{-1}$ obtained by IR spectroscopic analysis with a sample taken from the reaction mixture just before the addition of styrene. As a result of the calculation, it was found that the concentration of the reaction intermediate in the reaction mixture just before the addition of styrene was not less than 0.001 mol based upon 1 mol of TETA.

After completion of the dropwise addition of styrene, its interior temperature was maintained at 80° C. for 30 minutes.

Then, 23.4 g (1.3 mol) of distilled water as the amount of 10 times equal mole to the charged lithium amide was added thereto and stirred for 1 hour. Then, after separating precipitates in the reaction liquid in the flask by filtration, remained water was removed by vacuum distillation, whereby 991.2 g of an amino composition (F) was obtained as a reaction product. The content of unreacted styrene in the amino composition (F) was 0.4% by weight.

EXAMPLE 7

681.2 g (4.0 mol) of isophoronediamine, manufactured by Degussa AG (hereinafter, "IPDA") and 3.3 g (0.14 mol) of lithium amide were charged to a similar flask as the one used in Example 1, and its interior temperature was raised to 80° C. taking 15 minutes in a nitrogen gas stream with stirring.

Then, after stirring the reaction mixture for 120 minutes at 80° C., 416.8 g (4.0 mol) of styrene was added thereto dropwise continuously for 2.5 hours while keeping the temperature at 80° C.

The concentration of reaction intermediate in the reaction mixture was calculated from the absorption at 1573 cm$^{-1}$ obtained by IR spectroscopic analysis with a sample taken from the reaction mixture just before the addition of styrene. As a result of the calculation, it was found that the concentration of the reaction intermediate in the reaction mixture just before the addition of styrene was not less than 0.001 mol based upon 1 mol of IPDA.

After completion of the dropwise addition of styrene, its interior temperature was maintained at 80° C. for 120 minutes.

Then, 25.2 g (1.4 mol) of distilled water as the amount of 10 times equal mole to the charged lithium amide was added thereto and stirred. After separating precipitates in the reaction liquid in the flask by filtration, remained water was removed by vacuum distillation, whereby 1033.6 g of an amino composition (G) was obtained as a reaction product. The content of unreacted styrene in the amino composition (G) was 0.7% by weight and the content of unreacted IPDA was 14.6% by weight. The content of 1-addition product was 51.7% by weight, and the content of 2-addition product was 33.7% by weight.

EXAMPLE 8

617.2 g (4.0 mol) of norbornanediamine, manufactured by Mitsui Chemicals, Inc. (hereinafter, "NBDA") and 3.1 g (0.14 mol) of lithium amide were charged to a similar flask as the one used in Example 1, and its interior temperature was raised to 80° C. taking 15 minutes in a nitrogen gas stream with stirring.

Then, after stirring the reaction mixture for 120 minutes at 80° C., 416.8 g (4.0 mol) of styrene was added thereto dropwise continuously for 2.5 hours while keeping the temperature at 80° C.

The concentration of reaction intermediate in the reaction mixture was calculated from the absorption at 1575 cm$^{-1}$ obtained by IR spectroscopic analysis with a sample taken from the reaction mixture just before the addition of styrene. As a result of the calculation, it was found that the concentration of the reaction intermediate in the reaction mixture just before the addition of styrene was not less than 0.001 mol based upon 1 mol of NBDA.

After completion of the dropwise addition of styrene, its interior temperature was maintained at 80° C. for 120 minutes.

Then, 25.2 g (1.4 mol) of distilled water as the amount of 10 times equal mole to the charged lithium amide was added thereto and stirred. After separating precipitates in the reaction liquid in the flask by filtration, remained water was removed by vacuum distillation, whereby 971.2 g of an amino composition (H) was obtained as a reaction product. The content of unreacted styrene in the amino composition (H) was 0.7% by weight and the content of unreacted NBDA was 15.5% by weight.

EXAMPLE 9

460.0 g (2.0 mol) of polyoxypropylenediamine, manufactured by Huntsman Corporation, brand name; "JEFFAMINE D-230" (Molecular Weight; 230) and 21.3 g (0.93 mol) of lithium amide were charged to a similar flask as the one used in Example 1, and its interior temperature was raised to 100° C. taking 15 minutes in a nitrogen gas stream with stirring.

Then, after stirring the reaction mixture for 120 minutes at 100° C., 208.4 g (2.0 mol) of styrene was added thereto dropwise continuously for 4 hours while keeping the temperature at 100° C.

The concentration of reaction intermediate in the reaction mixture was calculated from the absorption at 1568 cm$^{-1}$ obtained by IR spectroscopic analysis with a sample taken from the reaction mixture just before the addition of styrene. As a result of the calculation, it was found that the concentration of the reaction intermediate in the reaction mixture just before the addition of styrene was not less than 0.001 mol based upon 1 mol of JEFFAMINE D-230.

After completion of the dropwise addition of styrene, its interior temperature was maintained at 100° C. for 120 minutes.

Then, 167.7 g (9.3 mol) of distilled water as the amount of 10 times equal mole to the charged lithium amide was added thereto and stirred. After separating precipitates in the reaction liquid in the flask by filtration, remained water was removed by vacuum distillation, whereby 635.1 g of an amino composition (I) was obtained as a reaction product. The content of unreacted styrene in the amino composition (I) was 0.9% by weight and the content of unreacted JEFFAMINE D-230 was 14.4% by weight.

EXAMPLE 10

296.0 g (2.0 mol) of polyoxyethylenediamine, manufactured by Huntsman Corporation, brand name; "JEFFAMINE EDR-148" (Molecular Weight; 148) and 1.5 g (0.065 mol) of lithium amide were charged to a similar flask as the one used in Example 1, and its interior temperature was raised to 100° C. taking 15 minutes in a nitrogen gas stream with stirring.

Then, after stirring the reaction mixture for 30 minutes at 100° C., 208.4 g (2.0 mol) of styrene was added thereto dropwise continuously for 2 hours while keeping the temperature at 100° C.

The concentration of reaction intermediate in the reaction mixture was calculated from the absorption at 1575 cm$^{-1}$ obtained by IR spectroscopic analysis with a sample taken from the reaction mixture just before the addition of styrene. As a result of the calculation, it was found that the concentration of the reaction intermediate in the reaction mixture just before the addition of styrene was not less than 0.001 mol based upon 1 mol of JEFFAMINE EDR-148.

After completion of the dropwise addition of styrene, its interior temperature was maintained at 100° C. for 30 minutes.

Then, 11.7 g (0.65 mol) of distilled water as the amount of 10 times equal mole to the charged lithium amide was added thereto and stirred. After separating precipitates in the reaction liquid in the flask by filtration, remained water was removed by vacuum distillation, whereby 479.1 g of an amino composition (J) was obtained as a reaction product. The content of unreacted styrene in the amino composition (J) was 0.2% by weight.

EXAMPLE 11

806.0 g (2.0 mol) of polyoxypropylenetriamine, manufactured by Huntsman Corporation, brand name; "JEFFAMINE T-403" (Molecular Weight; 403) and 35.0 g (1.5 mol) of lithium amide were charged to a similar flask as the one used in Example 1, and its interior temperature was raised to 100° C. taking 15 minutes in a nitrogen gas stream with stirring.

Then, after stirring the reaction mixture for 120 minutes at 100° C., 312.6 g (3.0 mol) of styrene was added thereto dropwise continuously for 6 hours while keeping the temperature at 100° C.

The concentration of reaction intermediate in the reaction mixture was calculated from the absorption at 1568 cm$^{-1}$ obtained by IR spectroscopic analysis with a sample taken from the reaction mixture just before the addition of styrene. As a result of the calculation, it was found that the concentration of the reaction intermediate in the reaction mixture just before the addition of styrene was not less than 0.001 mol based upon 1 mol of JEFFAMINE T-403.

After completion of the dropwise addition of styrene, its interior temperature was maintained at 100° C. for 120 minutes.

Then, 270.0 g (15.0 mol) of distilled water as the amount of 10 times equal mole to the charged lithium amide was added thereto and stirred. After separating precipitates in the reaction liquid in the flask by filtration, remained water was removed by vacuum distillation, whereby 1052.2 g of an amino composition (K) was obtained as a reaction product. The content of unreacted styrene in the amino composition (K) was 0.9% by weight.

COMPARATIVE EXAMPLE 1

817.2 g (6.0 mol) of MXDA and 2.9 g (0.13 mol) of lithium amide were charged to a similar flask as the one used in Example 1, and its interior temperature was raised to 80° C. taking 15 minutes in a nitrogen gas stream with stirring.

Then, immediately after the temperature of the reaction mixture was reached at 80° C., 625.2 g (6.0 mol) of styrene was added thereto dropwise continuously for 2 hours.

The concentration of reaction intermediate in the reaction mixture was calculated from the absorption at 1581 cm$^{-1}$ obtained by IR spectroscopic analysis with a sample taken from the reaction mixture just before the addition of styrene. As a result of the calculation, it was found that the concentration of the reaction intermediate in the reaction mixture just before the addition of styrene was less than 0.001 mol based upon 1 mol of MXDA.

After completion of the dropwise addition of styrene, its interior temperature was maintained to 80° C. for 60 minutes.

Then, 23.4 g (1.3 mol) of distilled water as the amount of 10 times equal mole to the charged lithium amide was added thereto and stirred. After separating precipitates in the reaction liquid in the flask by filtration, remained water was removed by vacuum distillation, whereby 1379.6 g of an amino composition (L) was obtained as a reaction product. The content of unreacted styrene in the amino composition (L) was 5.0% by weight.

COMPARATIVE EXAMPLE 2

681.0 g (5.0 mol) of MXDA and 3.3 g (0.14 mol) of lithium amide were charged to a similar flask as the one used in Example 1, and its interior temperature was raised to 80° C. taking 15 minutes in a nitrogen gas stream with stirring.

Then, immediately after the temperature of the reaction mixture was reached at 80° C., 651.3 g (6.25 mol) of styrene was added thereto dropwise continuously for 2.5 hours.

The concentration of reaction intermediate in the reaction mixture was calculated from the absorption at 1581 cm$^{-1}$ obtained by IR spectroscopic analysis with a sample taken from the reaction mixture just before the addition of styrene. As a result of the calculation, it was found that the concentration of the reaction intermediate in the reaction mixture just before the addition of styrene was less than 0.001 mol based upon 1 mol of MXDA.

After completion of the dropwise addition of styrene, its interior temperature was maintained to 80° C. for 60 minutes.

Then, 25.2 g (1.4 mol) of distilled water as the amount of 10 times equal mole to the charged lithium amide was added thereto and stirred. After separating precipitates in the reaction liquid in the flask by filtration, remained water was removed by vacuum distillation, whereby 1270.9 g of an amino composition (M) was obtained as a reaction product. The content of unreacted styrene in the amino composition (M) was 5.1% by weight.

COMPARATIVE EXAMPLE 3

853.2 g (6.0 mol) of 1,3-BAC and 3.0 g (0.13 mol) of lithium amide were charged to a similar flask as the one used in Example 1, and its interior temperature was raised to 80° C. taking 15 minutes in a nitrogen gas stream with stirring.

Then, immediately after the temperature of the reaction mixture was reached at 80° C., 625.2 g (6.0 mol) of styrene was added thereto dropwise continuously for 2 hours.

The concentration of reaction intermediate in the reaction mixture was calculated from the absorption at 1575 cm$^{-1}$ obtained by IR spectroscopic analysis with a sample taken from the reaction mixture just before the addition of styrene. As a result of the calculation, it was found that the concentration of the reaction intermediate in the reaction mixture just before the addition of styrene was less than 0.001 mol based upon 1 mol of 1,3-BAC.

After completion of the dropwise addition of styrene, its interior temperature was maintained to 80° C. for 120 minutes.

Then, 23.4 g (1.3 mol) of distilled water as the amount of 10 times equal mole to the charged lithium amide was added thereto and stirred. After separating precipitates in the reaction liquid in the flask by filtration, remained water was removed by vacuum distillation, whereby 1409.3 g of an amino composition (N) was obtained as a reaction product. The content of unreacted styrene in the amino composition (N) was 5.2% by weight.

White precipitates were found to be produced by mixing 10 parts by weight of the amino composition (N) with 100 parts by weight of methanol, which indicates that a polymer of styrene was formed as an unfavorable by-product.

COMPARATIVE EXAMPLE 4

711.0 g (5.0 mol) of 1,3-BAC and 3.4 g (0.15 mol) of lithium amide were charged to a similar flask as the one used in Example 1, and its interior temperature was raised to 80° C. taking 15 minutes in a nitrogen gas stream with stirring.

Then, immediately after the temperature of the reaction mixture was reached at 80° C., 651.3 g (6.25 mol) of styrene was added thereto dropwise continuously for 2.5 hours.

The concentration of reaction intermediate in the reaction mixture was calculated from the absorption at 1575 cm$^{-1}$ obtained by IR spectroscopic analysis with a sample taken from the reaction mixture just before the addition of styrene. As a result of the calculation, it was found that the concentration of the reaction intermediate in the reaction mixture just before the addition of styrene was less than 0.001 mol based upon 1 mol of 1,3-BAC.

After completion of the dropwise addition of styrene, its interior temperature was maintained to 80° C. for 120 minutes.

Then, 27.0 g (1.5 mol) of distilled water as the amount of 10 times equal mole to the charged lithium amide was added thereto and stirred. After separating precipitates in the reaction liquid in the flask by filtration, remained water was removed by vacuum distillation, whereby 1305.8 g of an amino composition (O) was obtained as a reaction product. The content of unreacted styrene in the amino composition (O) was 5.2% by weight.

White precipitates were found to be produced by mixing 10 parts by weight of the amino composition (O) with 100 parts by weight of methanol, which indicates that a polymer of styrene was formed as an unfavorable by-product.

COMPARATIVE EXAMPLE 5

412.7 g (4.0 mol) of DETA and 2.5 g (0.11 mol) of lithium amide were charged to a similar flask as the one used in Example 1, and its interior temperature was raised to 80° C. taking 15 minutes in a nitrogen gas stream with stirring.

Then, while sampling some of a reaction mixture, 651.3 g (6.25 mol) of styrene was added thereto dropwise continuously for 2.5 hours, immediately after the temperature of the reaction mixture was reached at 80° C.

The concentration of reaction intermediate was calculated from the absorption at 1572 cm$^{-1}$ obtained by IR spectroscopic analysis with a sample taken from the reaction mixture just before the addition of styrene. As a result of the calculation, it was found that the concentration of the reaction intermediate in the reaction mixture just before the addition of styrene was less than 0.001 mol based upon 1 mol of DETA.

After completion of the dropwise addition of styrene, its interior temperature was maintained to 80° C. for 30 minutes.

Then, 19.8 g (1.1 mol) of distilled water as the amount of 10 times equal mole to the charged lithium amide was added thereto and stirred. After separating precipitates in the reaction liquid in the flask by filtration, remained water was removed by vacuum distillation, whereby 777.0 g of an amino composition (P) was obtained as a reaction product. The content of unreacted styrene in the amino composition (P) was 5.1% by weight.

COMPARATIVE EXAMPLE 6

584.8 g (4.0 mol) of TETA and 3.0 g (0.13 mol) of lithium amide were charged to a similar flask as the one used in Example 1, and its interior temperature was raised to 80° C. taking 15 minutes in a nitrogen gas stream with stirring.

Then, immediately after the temperature of the reaction mixture was reached at 80° C., 651.3 g (6.25 mol) of styrene was added thereto dropwise continuously for 2.5 hours.

The concentration of reaction intermediate in the reaction mixture was calculated from the absorption at 1572 $cm^{-1}$ obtained by IR spectroscopic analysis with a sample taken from the reaction mixture just before the addition of styrene. As a result of the calculation, it was found that the concentration of the reaction intermediate in the reaction mixture just before the addition of styrene was less than 0.001 mol based upon 1 mol of TETA.

After completion of the dropwise addition of styrene, its interior temperature was maintained to 80° C. for 0.5 hours.

Then, 23.4 g (1.3 mol) of distilled water as the amount of 10 times equal mole to the charged lithium amide was added thereto and stirred. After separating precipitates in the reaction liquid in the flask by filtration, remained water was removed by vacuum distillation, whereby 990 g of an amino composition (Q) was obtained as a reaction product. The content of unreacted styrene in the amino composition (Q) was 5.4% by weight.

COMPARATIVE EXAMPLE 7

681.2 g (4.0 mol) of IPDA and 3.3 g (0.14 mol) of lithium amide were charged to a similar flask as the one used in Example 1, and its interior temperature was raised to 80° C. taking 15 minutes in a nitrogen gas stream with stirring.

Then, immediately after the temperature of the reaction mixture was reached at 80° C., 416.8 g (4.0 mol) of styrene was added thereto dropwise continuously for 2.5 hours.

The concentration of reaction intermediate in the reaction mixture was calculated from the absorption at 1573 $cm^{-1}$ obtained by IR spectroscopic analysis with a sample taken from the reaction mixture just before the addition of styrene. As a result of the calculation, it was found that the concentration of the reaction intermediate in the reaction mixture just before the addition of styrene was less than 0.001 mol based upon 1 mol of IPDA.

After completion of the dropwise addition of styrene, its interior temperature was maintained to 80° C. for 120 minutes.

Then, 25.2 g (1.4 mol) of distilled water as the amount of 10 times equal mole to the charged lithium amide was added thereto and stirred. After separating precipitates in the reaction liquid in the flask by filtration, remained water was removed by vacuum distillation, whereby 1032.7 g of an amino composition (R) was obtained as a reaction product. The content of unreacted styrene in the amino composition (R) was 10.8% by weight.

White precipitates were found to be produced by mixing 10 parts by weight of the amino composition (R) with 100 parts by weight of methanol, which indicates that a polymer of styrene was formed as an unfavorable by-product.

COMPARATIVE EXAMPLE 8

617.2 g (4.0 mol) of NBDA and 3.1 g (0.14 mol) of lithium amide were charged to a similar flask as the one used in Example 1, and its interior temperature was raised to 80° C. taking 15 minutes in a nitrogen gas stream with stirring.

Then, immediately after the temperature of the reaction mixture was reached at 80° C., 416.8 g (4.0 mol) of styrene was added thereto dropwise continuously for 2.5 hours.

The concentration of reaction intermediate in the reaction mixture was calculated from the absorption at 1575 $cm^{-1}$ obtained by IR spectroscopic analysis with a sample taken from the reaction mixture just before the addition of styrene. As a result of the calculation, it was found that the concentration of the reaction intermediate in the reaction mixture just before the addition of styrene was less than 0.001 mol based upon 1 mol of NBDA.

After completion of the dropwise addition of styrene, its interior temperature was maintained to 80° C. for 120 minutes.

Then, 25.2 g (1.4 mol) of distilled water as the amount of 10 times equal mole to the charged lithium amide was added thereto and stirred. After separating precipitates in the reaction liquid in the flask by filtration, remained water was removed by vacuum distillation, whereby 969.3 g of an amino composition (S) was obtained as a reaction product. The content of unreacted styrene in the amino composition (S) was 10.9% by weight.

White precipitates were found to be produced by mixing 10 parts by weight of the amino composition (S) with 100 parts by weight of methanol, which indicates that a polymer of styrene was formed as an unfavorable by-product.

COMPARATIVE EXAMPLE 9

460.0 g (2.0 mol) of JEFFAMINE D-230 and 21.3 g (0.93 mol) of lithium amide were charged to a similar flask as the one used in Example 1, and its interior temperature was raised to 100° C. taking 15 minutes in a nitrogen gas stream with stirring.

Then, immediately after the temperature of the reaction mixture was reached at 100° C., 208.4 g (2.0 mol) of styrene was added thereto dropwise continuously for 4 hours.

The concentration of reaction intermediate in the reaction mixture was calculated from the absorption at 1568 $cm^{-1}$ obtained by IR spectroscopic analysis with a sample taken from the reaction mixture just before the addition of styrene. As a result of the calculation, it was found that the concentration of the reaction intermediate in the reaction mixture just before the addition of styrene was less than 0.001 mol based upon 1 mol of JEFFAMINE D-230.

After completion of the dropwise addition of styrene, its interior temperature was maintained to 100° C. for 2 hours.

Then, 167.7 g (9.3 mol) of distilled water as the amount of 10 times equal mole to the charged lithium amide was added thereto and stirred. After separating precipitates in the reaction liquid in the flask by filtration, remained water was removed by vacuum distillation, whereby 635.0 g of an amino composition (T) was obtained as a reaction product. The content of unreacted styrene in the amino composition (N) was 37.7% by weight.

White precipitates were found to be produced by mixing 10 parts by weight of the amino composition (T) with 100 parts by weight of methanol, which indicates that a polymer of styrene was formed as an unfavorable by-product.

COMPARATIVE EXAMPLE 10

296.0 g (2.0 mol) of JEFFAMINE EDR-148 and 1.5 g (0.065 mol) of lithium amide were charged to a similar flask as the one used in Example 1, and its interior temperature was raised to 100° C. taking 15 minutes in a nitrogen gas stream with stirring.

Then, immediately after the temperature of the reaction mixture was reached at 100° C., 208.4 g (2.0 mol) of styrene was added thereto dropwise continuously for 4 hours.

The concentration of reaction intermediate in the reaction mixture was calculated from the absorption at 1575 cm$^{-1}$ obtained by IR spectroscopic analysis with a sample taken from the reaction mixture just before the addition of styrene. As a result of the calculation, it was found that the concentration of the reaction intermediate in the reaction mixture just before the addition of styrene was less than 0.001 mol based upon 1 mol of JEFFAMINE EDR-148.

After completion of the dropwise addition of styrene, its interior temperature was maintained to 100° C. for 30 minutes.

Then, 11.7 g (0.65 mol) of distilled water as the amount of 10 times equal mole to the charged lithium amide was added thereto and stirred. After separating precipitates in the reaction liquid in the flask by filtration, remained water was removed by vacuum distillation, whereby 478.8 g of an amino composition (U) was obtained as a reaction product. The content of unreacted styrene in the amino composition (N) was 5.9% by weight.

COMPARATIVE EXAMPLE 11

806.0 g (2.0 mol) of JEFFAMINE T-403 and 35.0 g (1.5 mol) of lithium amide were charged to a similar flask as the one used in Example 1, and its interior temperature was raised to 100° C. taking 15 minutes in a nitrogen gas stream with stirring.

Then, immediately after the temperature of the reaction mixture was reached at 100° C., 312.6 g (3.0 mol) of styrene was added thereto dropwise continuously for 6 hours.

The concentration of reaction intermediate in the reaction mixture was calculated from the absorption at 1568 cm$^{-1}$ obtained by IR spectroscopic analysis with a sample taken from the reaction mixture just before the addition of styrene. As a result of the calculation, it was found that the concentration of the reaction intermediate in the reaction mixture just before the addition of styrene was less than 0.001 mol based upon 1 mol of JEFFAMINE T-403.

After completion of the dropwise addition of styrene, its interior temperature was maintained to 100° C. for 120 minutes.

Then, 270.0 g (15.0 mol) of distilled water as the amount of 10 times equal mole to the charged lithium amide was added thereto and stirred. After separating precipitates in the reaction liquid in the flask by filtration, remained water was removed by vacuum distillation, whereby 1051.5 g of an amino composition (V) was obtained as a reaction product. The content of unreacted styrene in the amino composition (V) was 39.8% by weight.

White precipitates were found to be produced by mixing 10 parts by weight of the amino composition (V) with 100 parts by weight of methanol, which indicates that a polymer of styrene was comprised in the amino composition (V) as an unfavorable by-product.

As clear from the above Examples, the process for producing an amino composition of the present invention by addition reaction of a polyamine with an alkenyl group-containing compound wherein the polyamine is reacted preliminary with a strongly basic catalyst to produce a reaction mixture comprising reaction intermediate and then an alkenyl group-containing compound is added to the reaction mixture to proceed addition reaction provides an amino composition having stable properties.

What is claimed is:

1. A process for producing an amino composition by an addition reaction between a polyamine and an alkenyl group-containing compound in the presence of a strongly basic catalyst, which comprises:

conducting a preliminary reaction between a polyamine and a strongly basic catalyst to obtain a reaction mixture comprising a reaction intermediate, and adding an alkenyl group-containing compound to said reaction mixture comprising said reaction intermediate, after the concentration of said reaction intermediate in said reaction mixture becomes not less than 0.001 mol based upon 1 mol of said polyamine, to conduct an addition reaction.

2. The process according to claim 1, wherein the concentration of said reaction intermediate is calculated from the absorbance of an absorption peak obtained by an infrared spectroscopic analysis with said reaction mixture which had been observed at 1650 to 1580 cm$^{-1}$ before the preliminary reaction and then shifted to a position having 20 to 25 cm$^{-1}$ lower wavenumber after the preliminary reaction.

3. The process according to claim 1, wherein the reaction temperature of said preliminary reaction between a polyamine and a strong basic catalyst is 10 to 140° C. and the reaction time thereof is 20 to 360 minutes.

4. The process according to claim 1, wherein said alkenyl group-containing compound is added to said reaction mixture in the form of divided supply or in the form of continuous supply.

5. The process according to claim 4, wherein said alkenyl group-containing compound is added to said reaction mixture in the form of divided supply in 3 to 500 portions.

6. The process according to claim 4, wherein said alkenyl group-containing compound is added to said reaction mixture in the form of continuous supply taking 10 minutes to 20 hours.

7. The process according to claim 1, wherein said polyamine is selected from the group consisting of polyamines represented by the formula (1) wherein A is a phenylene group or a cyclohexylene group:

$$H_2N-CH_2\text{-}A\text{-}CH_2-NH_2 \qquad (1).$$

8. The process according to claim 1, wherein said polyamine is selected from the group consisting of polyamines represented by the formula (2) wherein n is 1 to 5:

$$H_2N-(CH_2CH_2NH)-_nH \qquad (2).$$

9. The process according to claim 1, wherein said polyamine is selected from the group consisting of cyclic aliphatic polyamines having at least nine carbon atoms, at least two amino groups and at least three active hydrogen atoms derived from said amino groups.

10. The process according to claim 1, wherein said polyamine is selected from the group consisting of polyoxyalkylenepolyamines.

11. The process according to claim 1, wherein said alkenyl group-containing compound is a compound having 2 to 10 carbon atoms.

12. The process according to claim 1, wherein the reaction temperature of said preliminary reaction between a polyamine and a strong basic catalyst is 10 to 140° C. and the reaction time thereof is 20 to 360 minutes.

13. The process according to claim 1, wherein said alkenyl group-containing compound is added to said reaction mixture in the form of divided supply or in the form of continuous supply.

14. The process according to claim 13, wherein said alkenyl group-containing compound is added to said reaction mixture in the form of divided supply in 3 to 500 portions.

15. The process according to claim 13, wherein said alkenyl group-containing compound is added to said reaction mixture in the form of continuous supply taking 10 minutes to 20 hours.

16. The process according to claim 1, wherein said polyamine is selected from the group consisting of polyamines represented by the formula (1) wherein A is a phenylene group or a cyclohexylene group:

$$H_2N\text{—}CH_2\text{-A-}CH_2\text{—}NH_2 \qquad (1).$$

17. The process according to claim 1, wherein said polyamine is selected from the group consisting of polyamines represented by the formula (2) wherein n is 1 to 5:

$$H_2N\text{—}(CH_2CH_2NH)\text{—}_nH \qquad (2).$$

18. The process according to claim 1, wherein said polyamine is selected from the group consisting of cyclic aliphatic polyamines having at least nine carbon atoms, at least two amino groups and at least three active hydrogen atoms derived from said amino groups.

19. The process according to claim 1, wherein said polyamine is selected from the group consisting of polyoxyalkylenepolyamines.

20. The process according to claim 1, wherein said alkenyl group-containing compound is a compound having 2 to 10 carbon atoms.

* * * * *